US006342647B1

(12) United States Patent
Roof et al.

(10) Patent No.: US 6,342,647 B1
(45) Date of Patent: Jan. 29, 2002

(54) VINYL MONOMER POLYMERIZATION INHIBITION USING HINDERED HYDROXYLAMINES

(75) Inventors: Glenn L. Roof, Sugar Land; Muslim D. Shahid, Houston, both of TX (US)

(73) Assignee: Baker Hughes Incorporated, Houston, TX (US)

( * ) Notice: Subject to any disclaimer, the term of this patent is extended or adjusted under 35 U.S.C. 154(b) by 0 days.

(21) Appl. No.: 09/391,970

(22) Filed: Sep. 8, 1999

Related U.S. Application Data

(60) Provisional application No. 60/099,634, filed on Sep. 9, 1998.

(51) Int. Cl.⁷ .................................................. C07C 7/20
(52) U.S. Cl. ........................ 585/5; 585/3; 585/4; 203/8
(58) Field of Search ........................... 585/3, 4, 5; 203/8

(56) References Cited

U.S. PATENT DOCUMENTS

| 3,849,498 | A | | 11/1974 | Sato et al. | 568/421 |
|---|---|---|---|---|---|
| 4,409,408 | A | * | 10/1983 | Miller | 585/4 |
| 4,434,307 | A | | 2/1984 | Miller | 585/4 |
| 4,465,882 | A | * | 8/1984 | Miller et al. | 585/4 |
| 4,797,504 | A | * | 1/1989 | Roling | 560/4 |
| 5,001,233 | A | | 3/1991 | Murray et al. | 540/29 |
| 5,258,138 | A | * | 11/1993 | Gatechair et al. | 252/403 |
| 5,290,888 | A | | 3/1994 | Gatechair et al. | 526/83 |
| 5,446,220 | A | * | 8/1995 | Arhancet | 585/5 |
| 5,489,720 | A | * | 2/1996 | Arhancet | 585/5 |
| 5,510,547 | A | * | 4/1996 | Arhancet et al. | 585/5 |
| 5,648,574 | A | * | 7/1997 | Arhancet et al. | 585/5 |
| 5,773,674 | A | * | 6/1998 | Arhancet et al. | 585/5 |
| 5,844,025 | A | * | 12/1998 | Cunkle et al. | 524/99 |
| 5,869,717 | A | * | 2/1999 | Frame et al. | 585/5 |
| 5,907,071 | A | * | 5/1999 | Arhancet | 585/5 |
| 6,024,894 | A | * | 2/2000 | Arhancet | 252/404 |
| 6,117,276 | A | * | 9/2000 | Cunkle et al. | 203/8 |
| 6,143,205 | A | * | 11/2000 | Sutoris et al. | 252/405 |
| 6,200,461 | B1 | * | 3/2001 | Eldin | 208/48 AA |

FOREIGN PATENT DOCUMENTS

| EP | 0467850 | 1/1992 |
|---|---|---|
| EP | 0685447 | 12/1995 |
| EP | 0690117 | 1/1996 |
| EP | 0761647 | 3/1997 |
| GB | 1337291 | 11/1973 |
| WO | WO 91/13619 | 9/1991 |

OTHER PUBLICATIONS

J. E. Baldwin, et al., "A General Procedure for the Synthesis of Isoxazolidin–5–ones", *Tetrahedron*, vol. 40, No. 21, Jan. 1, 1984, pp. 4363–4369.
*Chemical Abstracts* 79:54571, Sep. 10, 1973.

* cited by examiner

*Primary Examiner*—Ellen M. McAvoy
(74) *Attorney, Agent, or Firm*—Madan, Mossman & Sriram, P.C.

(57) ABSTRACT

It has been discovered that the polymerization of vinyl aromatic compounds, such as styrene, may be inhibited by the addition of a composition that contains a hindered hydroxylamine, and, optionally, a synergist together with the hindered hydroxylamine. In one embodiment of the invention, the hindered N,N-disubstituted hydroxylamine has the formula:

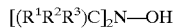

$$[(R^1R^2R^3)C]_2N{-}OH$$

where $R^1$, $R^2$, and $R^3$ are independently selected from the group consisting of hydrogen, straight, branched or cyclic alkyl, aryl, aralkyl, and alkaryl moieties; where no more than two of $R^1$, $R^2$, and $R^3$ on each C can be hydrogen at a time; where one or more of $R^1$, $R^2$, and $R^3$ on one C may be joined to a $R^1$, $R^2$, and $R^3$ on the other C to form a cyclic moiety selected from the group consisting of alkylene, and aralkylene moieties; where any two of the $R^1$, $R^2$, and $R^3$ on any one C may be joined together to form a cycloalkyl; where any of the above definitions of $R^1$, $R^2$, and $R^3$ may contain one or more heteroatoms selected from the group consisting of N, O and S; and where the total number of carbon atoms in the hindered N,N-disubstituted hydroxylamine ranges from 6 to 70. Optional synergists may include alkyl-substituted hydroxyarenes such as 2,5-di-tert-butylhydroquinone, and hydrogen transfer agents such as 1,2,3,4-tetrahydronaphthalene; and the like, and mixtures thereof.

6 Claims, No Drawings

VINYL MONOMER POLYMERIZATION INHIBITION USING HINDERED HYDROXYLAMINES

This Application claims benefit to Provisional Application No. 60/099,634 filed Sep. 9, 1998.

FIELD OF THE INVENTION

The present invention relates to methods and compositions for inhibiting the polymerization of vinyl monomers, and more particularly relates, in one embodiment, to methods and compositions for inhibiting the polymerization of vinyl aromatic monomers.

BACKGROUND OF THE INVENTION

It is well known that undesirable and costly polymerization is a significant problem during the manufacturing of various vinyl monomers, particularly vinyl aromatic compounds, such as styrene. Many kinds of inhibitors have been used in the past to minimize this problem. For instance, inhibitors such as diethylhydroxylamine, phenyl-p-phenylenediamines, tert-butyl catechol, and phenothiazine have been used to control polymer formation. During the early 1980s, compounds selected from the groups called alkyl-substituted di-nitro-phenols and nitroso-phenols found widespread use in the styrene industry. However, because such compounds also functioned as insecticides or were dangerous to handle, their use has been discouraged by environmental and government agencies.

The literature contains references of N,N-disubstituted hydroxylamines as good free radical scavengers, for example diethylhydroxylamine.

Recently, a new class of compounds called stable free radicals is being investigated to replace the nitrophenol products. The literature is replete with examples of "hindered nitroxides" as excellent free radical scavengers. Perhaps the most well known such nitroxide used for scavenging free radicals is 2,2,6,6-tetramethyl-1-piperidinyloxy. Although stable free radicals effectively inhibit monomer polymerization, their current cost makes them unattractive. It would be desirable if a composition and method could be devised to overcome some of the problems of the commercial polymerization inhibitors.

SUMMARY OF THE INVENTION

Accordingly, it is an object of the present invention to provide a method and composition to effectively inhibit the polymerization of vinyl compounds, such as styrene.

It is another object of the present invention to provide a method and composition to effectively inhibit the polymerization of styrene that is less expensive than using stable free radicals exclusively.

Still another object of the invention is to permit use of a composition to effectively inhibit the polymerization of styrene that has little or no environmental concerns.

In carrying out these and other objects of the invention, there is provided, in one form, a composition for inhibiting polymerization of vinyl compounds comprising a hindered N,N-disubstituted hydroxylamine having the formula:

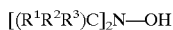

where $R^1$, $R^2$, and $R^3$ are independently selected from the group consisting of hydrogen, straight, branched or cyclic alkyl, aryl, aralkyl, and alkaryl moieties; where no more than two of $R^1$, $R^2$, and $R^3$ on each C can be hydrogen at a time; where one or more of $R^1$, $R^2$, and $R^3$ on one C may be joined to a $R^2$, $R^2$, and $R^3$ on the other C to form a cyclic moiety selected from the group consisting of alkylene, and aralkylene moieties; where any two of the $R^1$, $R^2$, and $R^3$ on any one C may be joined together to form a cycloalkyl; where any of the above definitions of $R^1$, $R^2$, and $R^3$ may contain one or more heteroatoms selected from the group consisting of N, O and S; and where the total number of carbon atoms in the hindered N,N-disubstituted hydroxylamine ranges from 6 to 70.

DETAILED DESCRIPTION OF THE INVENTION

It has been discovered that hindered N,N-disubstituted hydroxylamines are an effective treatment to control styrene monomer polymerization. This treatment protocol is most effective when formulated together with synergists such as 2,5-di-tert-butylhydroquinone, 1,2,3,4-tetrahydronaphthalene, and the like.

The hindered N,N-disubstituted hydroxylamines are expected to be useful in inhibiting the polymerization of a variety of vinyl monomers including, but not necessarily limited to, styrene, acrylonitrile, acrylic acid, methacrylic acid, vinyl chloride, acrylates, methacrylates, vinyl ethers, butadiene, isoprene, and the like. It is particularly expected that suitable vinyl aromatic monomers that may be polymerization inhibited by the compositions and methods of this invention include, but are not necessarily limited to, styrene, substituted styrene such as α-methylstyrene, divinylbenzene, vinyltoluene, vinyl naphthalene, and isomers thereof. Preferably, the aromatic monomer is styrene. By "substituted styrenes" is meant styrene substituted with alkyl, aryl, aralkyl, alkaryl hydrocarbon moieties optionally containing oxygen, nitrogen and sulfur, and mixtures thereof. In one non-limiting embodiment, these hydrocarbon substituents have from 1 to 20 carbon atoms, preferably from 1 to 8 carbon atoms, and most preferably from 1 to 4 carbon atoms.

Hindered N,N-Disubstituted Hydroxylamines

Hindered N,N-disubstituted hydroxylamines expected to be effective in the method of this invention include, but are not limited to, those of the formula:

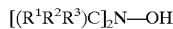

where $R^1$, $R^2$, and $R^3$ are independently selected from the group consisting of hydrogen, straight, branched or cyclic alkyl, aryl, aralkyl, and alkaryl moieties; where only one of $R^1$, $R^2$, and $R^3$ on each C can be hydrogen at a time; where one or more of $R^1$, $R^2$, and $R^3$ on one C may be joined to a $R^1$, $R^2$, and $R^3$ on the other C to form a cyclic moiety selected from the group consisting of alkylene, and aralkylene moieties; where any two of the $R^1$, $R^2$, and $R^3$ on any one C may be joined together to form a cycloalkyl; where any of the above definitions of $R^1$, $R^2$, and $R^3$ may contain one or more heteroatoms selected from the group consisting of N, O and S; and where the total number of carbon atoms in the hindered N,N-disubstituted hydroxylamine ranges from 6 to 70. Preferably, the total number of carbon atoms in the hindered N,N-disubstituted hydroxylamine ranges from 8 to 20, and where the hydrocarbon groups (alkyl aryl, aralkyl, alkaryl, and cyclic moieties) may contain oxygen moieties. In another preferred embodiment of the invention, $R^1$, $R^2$, and $R^3$ independently and individually contain from 1–10 carbon atoms, preferably from 1–8 carbon atoms, more preferably from 1–6 carbon atoms and most preferably from 1–4 carbon atoms. This definition of the hindered N,N-disubstituted hydroxylamines is understood to include structures having functional groups and substituents including, but not necessarily limited to, ether groups, hydroxyl groups, amine groups, carbonyl groups, cyano groups, ester groups, sulfone groups, sulfoxide groups, sulfide groups, and the like.

Some specific, non-limiting examples of suitable hindered N,N-disubstituted hydroxylamines include, but are not necessarily limited to, compounds of the following structures:

III
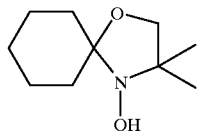

V
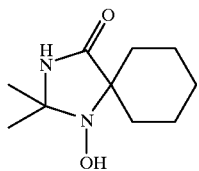

VI
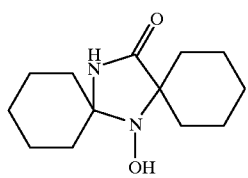

VII
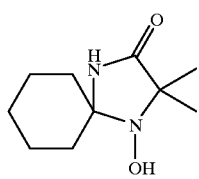

VIII
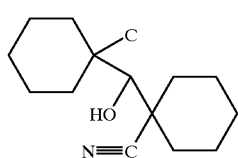

IX
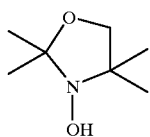

X
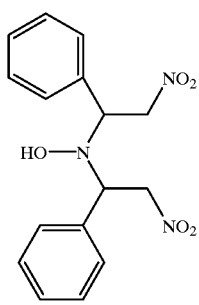

-continued

XI
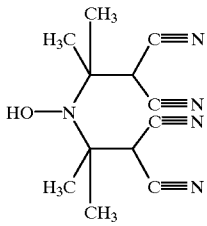

Synthesis of Compounds of Structures X and XI

It is believed that a novel Michael-type addition preparation method for making hindered hydroxylamines of the structure such as X and XI has been discovered. This method has two embodiments, the first of which may be described as Synthesis A:

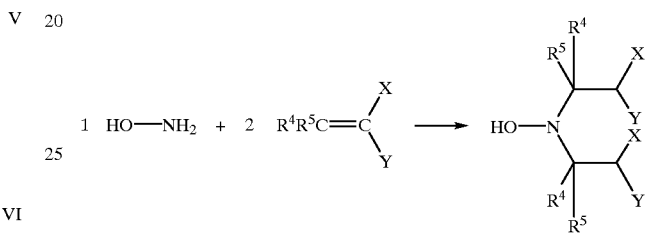

where X and Y are hydrogen or the same or different electron withdrawing group and include, but are not necessarily limited to: $-NO_2$, $-C\equiv N$,

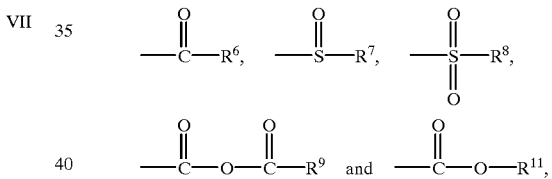

where $R^4$, $R^5$, $R^6$, $R^7$, $R^8$, $R^9$, and $R^{11}$ can independently be the same as $R^1$, $R^2$ and $R^3$, except that both $R^4$ and $R^5$ may be simultaneously hydrogen; and as long as both X and Y are not simultaneously hydrogen, that is, at least one of X or Y must be an electron withdrawing group.

In one example using Synthesis A, $R^4$ and $R^5$ are both methyl and X and Y are cyano.

The second embodiment may be described as Synthesis B:

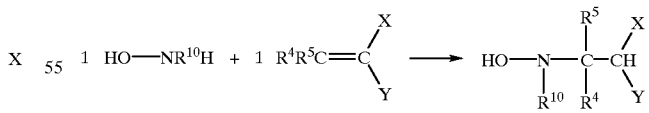

where X, Y and $R^4$ and $R^5$ are as above and $R^{10}$ is $-C(R^7)_3$, where $R^7$ is as defined above.

An example of using Synthesis B would be as follows:

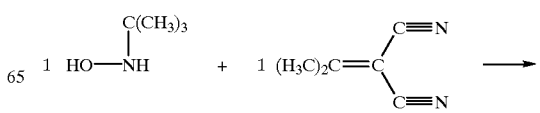

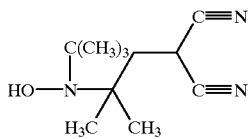

Synergists

Suitable synergists that may optionally be included in the polymerization inhibitor composition of this invention include, but are not limited to substituted alkyl-dihydroxyarenes (e.g., alkylphenols), nitrophenols (including, but not necessarily limited to dinitro-o-cresol and dinitro-sec-butylphenol), hydrogen transfer agents, and the like, and mixtures thereof.

Alkylhydroxyarenes

Suitable substituted alkyl-mono- and alkyl-di-hydroxyarenes for the polymerization inhibiting composition of the invention may include, but are not necessarily limited to, substituted alkylhydroxybenzenes having the formula:

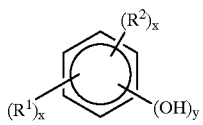

where $R^1$ and $R^2$ are the same or different and are independently selected from the group consisting of hydrogen, straight, branched, and cyclic alkyl groups averaging from about 1 to about 6 carbon atoms, preferably from about 1 to about 4 carbon atoms, and where x averages from about 1 to about 3, and where y averages from about 1 to 2.

Examples of specific substituted alkylhydroxyarenes that would be suitable in the composition of this invention include, but are not necessarily limited to, 2,6-di-tert-butylphenol; tert-butylhydroquinone; 2,5-di-tert-butylhydroquinone; tert-butylcatechol; hydroquinone; 3,5-di-tert-butylcatechol; catechol; 3,3,3',3'-tetramethyl-1,1'-spiro-bis-indane-5,5',6,6'-teterol; and mixtures thereof.

Hydrogen Transfer Agents

It is anticipated that any compound which readily donates hydrogen would be expected to be useful. Hydrogen transfer agents suitable for use in the polymerization inhibiting composition of this invention include, but are not necessarily limited to, naphthalene; anthracene; decalin; hydroquinoline; 1,2,3,4-tetrahydronaphthalene (TETRALIN®; DuPont); 9,10-dihydroanthracene; fluorene; squalane; squalene; tetramethylhydroquinoline; and mixtures thereof.

Proportions

A number of factors affect the effective amount of the hindered hydroxylamines of this invention that would be useful to inhibit the polymerization of a vinyl compound, including, but not necessarily limited to, the nature of the compound, the concentration of the compound, the temperature and pressure environment of the compound, the nature of the particular hindered hydroxylamine used, whether or not a synergist is present, the ratio of the synergists, and the like. The invention is not limited to inhibiting polymerization of vinyl compounds in particular temperature and pressure environments. Nevertheless, some general guidelines as to the effective proportion of the hindered hydroxylamines in the vinyl compound may be given.

For instance, the amount of hindered N,N-disubstituted hydroxylamine in the vinyl compound may range from about 5 to about 1,000 ppm, preferably from about 100 to about 400 ppm, based on the total amount of vinyl compound. If a synergist is employed, the amount of each synergist present ranges from about 0 to about 400 ppm, preferably from about 5 to about 400 ppm, most preferably from about 50 to about 300 ppm, again, based on the total amount of vinyl compound.

If multiple components are employed, the components of the composition may be simply mixed together. They may be mixed together in a single composition prior to addition to the vinyl aromatic compound, although they may also be added to the vinyl compound separately as well.

One non-limiting idea about a possible reaction mechanism of the hindered hydroxylamines of the present invention to inhibit polymerization would be generally shown as follows:

$$R_2N-OH + R\cdot \rightarrow R_2N-O\cdot + R-H \qquad (I)$$

where R· is a growing free radical polymer chain. When the above reaction (I) occurs, the polymerization is inhibited because now polymerization initiation must occur all over again and when it does, the above scavenging reaction can occur again.

The invention will be further illustrated with respect to specific examples, which are not intended to limit the invention, but rather to more fully describe it.

EXAMPLE 1

Preparation

It was initially desired to make the nitroxide of structure (IV) according to the following reaction:

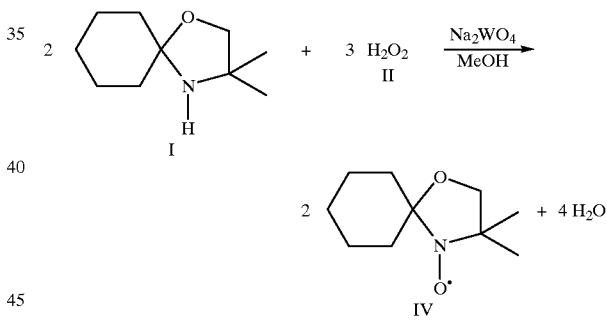

The following reactants were employed:

| | | |
|---|---|---|
| oxazolidine, I | 8.45 g | 50 mmol |
| 31% $H_2O_2$, II | 11.0 g | 100 mmol |
| $Na_2WO_4 \cdot 2H_2O$ | 0.469 g | 1.4 mmol |
| $CH_3OH$ | 11.0 g | |
| $H_2O$ | 6 g (added to partially solubilize the $Na_2WO_4$) | |

To a 50 ml, 3-necked, mini-lab flask, fitted with a thermometer, an addition funnel and a spin bar were charged 8.45 g of oxazolidine, 0.469 g of sodium tungstate ($Na_2WO_4 \cdot 2H_2O$), 11 g of methanol and 6 g of DI water. The 11.0 g of 31% hydrogen peroxide were added dropwise over a 75 minute at room temperature. Heat evolved and the contents were stirred for about an hour. After standing for a time, crystals precipitated, which were recrystallized and washed to give off-white crystals which turned out to be the hindered hydroxylamine of structure III:

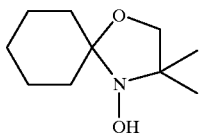

III

EXAMPLES 2–8

Test Method

To evaluate the hindered hydroxylamine of structure III as a polymerization inhibitor for styrene, the constant nitrogen flow reflux test method was used. Past laboratory data suggests that this test method best prevents the presence of residual oxygen in the reaction vessels during testing. Oxygen has been shown in the literature and laboratory results to increase the activity of some inhibitors in preventing styrene monomer polymerization.

Inhibited styrene monomer purchased from Aldrich Chemicals was distilled under vacuum (45° C., 29 mm Hg) to remove the conventional storage inhibitor 4-tert-butyl-pyrocatechol. The distilled styrene was checked for polymer content by sampling a portion and mixing in cold methanol. The distillation of the styrene monomer is considered successful if the two liquids mix completely with no presence of haze or cloudy appearance. One hundred mls of distilled styrene was transferred into a 250 ml, three-necked, round bottom reaction flask. The desired amount of inhibitor(s) were added to the distilled styrene monomer. The reaction flask was also equipped with a condenser, a thermocouple (type J), thermometer (Celsius), and a gas sparge tube.

The reaction apparatus was placed in an oil bath. The temperature of the oil bath could be raised by the use of an external heating device. The styrene monomer was purged with nitrogen for 20 minutes to insure that the effect of oxygen on styrene monomer and/or inhibitors would be insignificant during the test run. While continuing the nitrogen purge, the temperature of the oil bath and subsequently, the styrene/inhibitor(s) composition was raised until a styrene monomer/inhibitor(s) composition temperature of 118° C.±2° C. was obtained. The styrene monomer/inhibitor(s) composition was maintained under these conditions for 90 minutes.

The reaction flask apparatus was removed from the hot oil bath and the styrene monomer/inhibitor(s) composition was allowed to cool to ambient under continuing nitrogen purge. The styrene monomer/inhibitor(s) composition was transferred from the reaction flask into a 1000 ml beaker containing 200 ml of cold methanol. The styrene/methanol mixture was mixed until the polymer, if any, agglomerates. Eight hundred ml of n-heptane was added to the styrene methanol composition. The polystyrene, if any, was allowed to settle out of solution until the liquid phase of the composition was clear. The styrene/methanol/n-heptane/polymer mixture was filtered through a 1.0 μm glass fiber filter. Any remaining polymer was washed from the beaker with n-heptane through the glass fiber filter paper. The filter paper was placed into an oven with ventilation capable of maintaining a temperature of 150° C.±2° C. for 16 hours. The dried polymer was cooled in a desiccator, and the weight of the polymer was obtained by taking the difference of the weight of filter paper/polymer minus the initial weight of filter paper. Results were reported as mgs of polymer per 100 ml of styrene.

Table I summarizes the results from the initial testing.

TABLE I

Polymerization Inhibition Using Various Inhibitors

| Ex. | Inhibitor | Active dosage (ppm) | Synergists | Total synergist dosage (ppm)* | Polymer (mg/100 ml) |
|---|---|---|---|---|---|
| 2 | 4-OH TEMPO | 125 | N | — | 6000 |
| 3 | 4-OH TEMPO | 500 | N | — | 2500 |
| 4 | Str. III** | 400 | N | — | 3800 |
| 5 | 4-OH TEMPO | 125 | Y | 250 | 50 |
| 6 | Str. III | 125 | Y | 250 | 1900 |
| 7 | None | — | Y | 250 | 14,000 |
| 8 | Blank | — | N | — | 35,000 |

4-OH TEMPO = 2,2,6,6-tetramethyl-1-piperidinyloxy, a stable nitroxide
*Synergists were 125 ppm each of 2,5-di-tert-butylhydroquinone and 1,2,3,4-tetrahydronaphthalene
**Structure III hindered hydroxylamine While 4-OH TEMPO with synergists gives better results as compared with the hindered hydroxylamine compound of structure III with synergists under equal conditions, it must be remembered that the hindered hydroxylamine of the invention is considerably less expensive than TEMPO, and would thus be commercially competitive. Example 6 with synergists outperformed 4-OH TEMPO alone, as seen in Examples 2 and 3.

EXAMPLES 9–11

Examples 9–11 were conducted similarly to Examples 2–8, except that the Structure X compound (Example 11) was compared with a blank (Example 9) and 4-hydroxy TEMPO (4-OH TEMPO). Table II summarizes the results from the initial testing.

TABLE I

Polymerization Inhibition Using Various Inhibitors

| | | | | % Polymer normalized per: | |
|---|---|---|---|---|---|
| Ex. | Inhibitor | Dose (ppm) | % Polymer | 150 ppm additive | 1 equivalent of additive |
| 9 | Blank | — | 36 | — | — |
| 10 | 4-OH TEMPO | 150 | 4 | 4 | 3.5 |
| 11 | Str. X | 173 | 11 | 13 | 5.9 |

On a weight basis 4-OH TEMPO out performed the compound of Structure X by 3 to 1, but on a per equivalent basis 4-OH TEMPO out performed the compound of Structure X by only 1.7 to 1. Thus, on a performance/ cost basis, the compound of Structure X should be superior to 4-OH TEMPO.

In the foregoing specification, the invention has been described with reference to specific embodiments thereof, and has been demonstrated as effective in providing a composition for inhibition of polymerization of vinyl aromatic compounds, such as styrene. However, it will be evident that various modifications and changes can be made thereto without departing from the broader spirit or scope of the invention as set forth in the appended claims. Accordingly, the specification is to be regarded in an illustrative rather than a restrictive sense. For example, specific hindered hydroxylamines and/or combinations of certain hydroxylamines with synergists, other than those specifically tried, in other proportions or added in different ways, falling within the claimed parameters, but not specifically identified or tried in a particular composition to improve the polymerization inhibition herein, are anticipated to be within the scope of this invention.

We claim:

1. A composition for inhibiting polymerization of vinyl compounds comprising a hindered N,N-disubstituted hydroxylamine having the formula:

$$[(R^1R^2R^3)C]_2N\text{—}OH$$

where $R^1$, $R^2$, and $R^3$ are independently selected from the group consisting of hydrogen straight, branched or cyclic alkyl, aryl, aralkyl, and alkaryl moieties;

where only one of $R^1$, $R^2$, and $R^3$ on each C can be hydrogen at a time;

where one or more of $R^1$, $R^2$, and $R^3$ on one C may be joined to a $R^1$, $R^2$, and $R^3$ on the other C to form a cyclic moiety selected from the group consisting of alkylene, and aralkylene moieties;

where any two of the $R^1$, $R^2$, and $R^3$ on any one C may be joined together to form a cycloalkyl;

where any of the above definitions of $R^1$, $R^2$, and $R^3$ may contain one or more heteroatoms selected from the group consisting of N, O and S; and where the total number of carbon atoms in the hindered N,N-disubstituted hydroxylamine ranges from 6 to 70 and a synergist selected from the group consisting of 2,5-di-tert-butylhydroquinone, 1,2,3,4-tetrahydronaphthalene, and mixtures thereof.

2. A method for inhibiting polymerization of vinyl compounds comprising:

providing a vinyl compound; and adding thereto an amount effective to inhibit polymerization of the vinyl aromatic compound of a composition comprising a hindered N,N-disubstituted hydroxylamine having the formula:

$$[(R^1R^2R^3)C]_2N\text{—}OH$$

where $R^1$, $R^2$, and $R^3$ are independently selected from the group consisting of hydrogen, straight, branched or cyclic alkyl, aryl, aralkyl, and alkaryl moieties;

where only one of $R^1$, $R^2$, and $R^3$ on each C can be hydrogen at a time;

where one or more of $R^1$, $R^2$, and $R^3$ on one C may be joined to a $R^1$, $R^2$, and $R^3$ on the other C to form a cyclic moiety selected from the group consisting of alkylene, and aralkylene moieties;

where any two of the $R^1$, $R^2$, and $R^3$ on any one C may be joined together to form a cycloalkyl;

where any of the above definitions of $R^1$, $R^2$, and $R^3$ may contain one or more heteroatoms selected from the group consisting of N, O and S; and where the total number of carbon atoms in the hindered N,N-disubstituted hydroxylamine ranges from 6 to 70 and a synergist selected from the group consisting of 2,5-di-tert-butylhydroquinone, 1,2,3,4-tetrahydronaphthalene, and mixtures thereof.

3. The method of claim 2 where in the adding, the amount of hindred N,N-disubstituted hydroxylamine in the vinyl compound ranges from about 5 to about 1,000 ppm.

4. The method of claim 2 where in the adding, the amount of hindered N,N-disubstituted hydroxylamine in the vinyl compound ranges from about 5 to 1000 ppm, and the amount of each synergist present ranges from about 25 to about 400 ppm.

5. The method of claim 2 where in the providing, the vinyl compound is an aromatic vinyl compound.

6. The method of claim 4 where in the providing, the vinyl compound is selected from the group consisting of styrene, acrylonitrile, acrylic acid, methacrylic acid, vinyl chloride, acrylates, methacrylates, vinyl ethers, butadiene, and isoprene.

* * * * *